United States Patent [19]
Law et al.

[11] Patent Number: 5,302,753
[45] Date of Patent: Apr. 12, 1994

[54] ANILIDE COUPLERS FOR PHOTOGENERATING PIGMENTS

[75] Inventors: Kock-Yee Law, Penfield; Ihor W. Tarnawskyj, Rochester, both of N.Y.

[73] Assignee: Xerox Corporation, Stamford, Conn.

[21] Appl. No.: 955,192

[22] Filed: Oct. 1, 1992

[51] Int. Cl.$^5$ .................................. C07C 237/20
[52] U.S. Cl. ............................................ 564/173
[58] Field of Search ............... 548/420; 564/172, 173; 430/135; 106/496

[56] References Cited

U.S. PATENT DOCUMENTS

| | | | |
|---|---|---|---|
| 4,418,133 | 11/1983 | Katagiri et al. | 430/58 |
| 4,480,019 | 10/1984 | Higashiguchi et al. | 430/58 |
| 4,571,369 | 2/1986 | Yamashita | 430/56 |
| 4,713,307 | 12/1987 | Law et al. | 430/57 |
| 4,797,337 | 1/1989 | Law et al. | 430/58 |
| 4,830,943 | 5/1989 | Sasaki et al. | 430/58 |
| 5,130,443 | 7/1992 | Law et al. | 548/420 |

Primary Examiner—John Kight, III
Assistant Examiner—Richard Jones
Attorney, Agent, or Firm—E. O. Palazzo

[57] ABSTRACT

Disclosed is the anilide coupler 2,8-dihydroxy-3-naphthanilide; and the anilide coupler of the formula

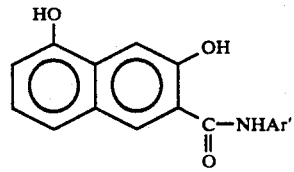

wherein Ar' is an aromatic group.

6 Claims, 4 Drawing Sheets

ANILIDE COUPLERS FOR PHOTOGENERATING PIGMENTS

BACKGROUND OF THE INVENTION

This invention is generally directed to novel anilide couplers, and processes for the preparation thereof. More specifically, the present invention is directed to anilide couplers which can be selected for the preparation of photogenerating pigments, especially photogenerating azo pigments which are sensitive to red and near infrared wavelengths, when these pigments are incorporated into imaging members such as xerographic imaging members comprised of a supporting substrate, the aforementioned photogenerating azo pigments, and a charge transport layer. In one embodiment, thus the present invention is directed to anilide coupler obtained from 2,8-dihydroxy-3-naphthoic acid, reference U.S. Pat. No. 5,130,443, the disclosure of which is totally incorporated herein by reference, for obtaining photogenerating azo pigments wherein these pigments absorb light beyond 400 to 650 nanometers of traditional azo pigments of the prior art, and more specifically, wherein the azo pigments prepared from the anilide couplers of the present invention absorb in the wavelength region of from 650 to 850 nanometers. Thus, in embodiments the present invention is directed to novel couplers and processes thereof, which couplers can be utilized to prepare photogenerating pigments in an economical manner. Also, with the present invention there can be prepared bisazo, trisazo and similar photogenerating pigments from the couplers illustrated herein.

The anilide couplers can be prepared from 2,8-dihydroxy-3-naphthoic acid. In one embodiment, the process comprises the reaction of 2,8-dihydroxy-3-naphthoic acid, an aromatic hydroxy compound, such as phenol, and a catalyst like phosphorous oxychloride, separating the resulting 2,8-dihydroxy-3-naphthoate, thereafter reacting the naphthoate with aniline in the presence of a solvent like N-methyl pyrrolidinone, and isolating the product 2,8-dihydroxy-3-naphthanilide. The resulting anilide can then be reacted as illustrated herein to provide azo, bisazo, trisazo, and the like photogenerating pigments which are sensitive to red and infrared light enabling their use in imaging members selected for electrophotographic imaging and printing systems, especially wherein light emitting diodes and diode lasers are utilized. More specifically, the couplers resulting with the processes of the present invention can be selected for the preparation of azo photogenerating pigments, reference for example U.S. Pat. Nos. 4,916,039 and 4,925,758, the disclosures of which are totally incorporated herein by reference. The aforementioned photogenerating pigments can be selected for layered photoresponsive imaging members comprised of a charge transport layer, a photogenerating layer and a supporting substrate. More specifically, the photogenerating pigments that can be obtained with the processes of the present invention can be selected for layered photoconductive imaging members with improved xerographic properties, inclusive of high charge acceptance, low dark decay, high photosensitivity, including photosensitivity in the wavelength regions of from about 650 to about 850 nanometers, enabling their selection for electrophotographic, especially xerographic imaging systems, LED printers, and diode laser printers. The imaging members can be comprised of photoconductive layers comprised of the photogenerating pigments and thereover charge or hole transport layers, especially those comprised of aryl amines, which members can be sensitive to light in the wavelength region of from about 750 to about 850 nanometers. The resulting members are responsive to red and near infrared illumination originating from laser printing apparatuses wherein, for example, gallium arsenide diode lasers are selected. The photoresponsive imaging members can also, for example, contain, situated between a photogenerating layer and a hole transporting layer, or situated between a photogenerating layer and a supporting substrate with a charge transport layer in contact with the photogenerating layer, a photoconductive composition comprised of the photogenerating azo pigments.

Examples of advantages associated with the processes of the present invention include the provision of couplers that enable infrared sensitive photogenerating pigments; obtaining couplers with high purity, for example from about 95 to about 99 percent or higher in embodiments; immediate utilization of the couplers obtained for the preparation of bisazo photogenerating pigments; scale up to manufacturing conditions is enabled in embodiments thereof; the products obtained can be, after synthesis, selected for the preparation of photogenerating azo pigments, and wherein the resulting xerographic properties of the photoconductive members such as dark decay, charge acceptance, and charge stability are acceptable; and the like. Two important advantages associated with the present invention are that the photogenerating pigments obtained absorb at longer wavelengths as compared to, for example, azo pigments obtained from couplers without the 8-position hydroxy; and that the processes are very econimical especially as compared to obtaining photogenerating pigments from the anilide couplers of 2-hydroxy-11H-benzo(a)carbazole-3-carboxylic acid.

The preparation by certain method of anilide couplers is known. More specifically, there is disclosed in Japanese Laid Open 59-137459, 1984, the preparation of 2-hydroxy-11H-benzo(a)carbazole-3-carbohydrozide by initially preparing a methyl ester (methyl 2-hydroxy-11H-benzo(a)carbazole-3-carboxylate) and condensing this ester with a hydrazine. Also, in the Color Index, Third Edition, Volume 4, published by the Society of Dyes and Colorants, there is illustrated the preparation of methoxy anilides, such as 2-hydroxy-11H-benzo(a)-carbazole-3-carbox-2'-methyl-4'-methoxyanilide, by the condensation of an acid with an appropriate aniline. Other representative prior art disclosing the preparation of couplers include U.S. Pat. Nos. 4,916,039 and 4,925,758 wherein there is illustrated the conversion of an appropriate acid to an acid halide such as acid chloride, and subsequently reacting the resulting acid halide with an aniline to obtain an anilide coupler.

In a patentability search report there were located U.S. Pat. Nos. 4,418,133; 4,480,019; 4,571,369 and 4,713,307.

Also, many processes are known for the preparation of azo photogenerating pigments, such as azotization and coupling, reference U.S. Pat. No. 3,898,084. Examples of aromatic amines selected for the preparation of azo pigments include 2,7-diaminofluorenone, reference for example, U.S. Pat Nos. 4,797,337; 4,830,924; 4,822,705; 4,596,754; 4,618,672; 4,481,271; 4,400,455; 4,390,608; 4,327,176; 4,314,015; 4,299,015; 4,299,896 and 4,551,404 possess in many instances high sensitivity and high electrical stability. Azo pigments synthesized from anilide couplers of 2-hydroxy-11H-benzo(a)carbazole-3-carboxylic acid enable imaging members with photoresponses at longer wavelengths, for example beyond 650 nanometers.

In U.S. Pat. No. 4,916,039 there are disclosed photoconductors with charge generating pigments comprised of certain azo compounds, reference the formula illustrated in the Abstract of the Disclosure, and in column 3. The aforementioned azo pigments are prepared by the coupling reaction of 2-hydroxy-3-carbamoylbenzo-alpha-carbazole derivatives of Formula VI with diazonium salts, reference columns 6 and 7. The coupling reaction is accomplished by dissolving the diazonium salts and a coupler, such as those obtained with the processes of the present invention, in an organic solvent, such as DMF and DMSO, and adding dropwise thereto an alkaline aqueous solution at a temperature of from about −10 to about 40° C., see column 7 for example. A similar teaching is present in U.S. Pat. No. 4,925,758.

Imaging members with certain bisazo pigments are known, reference for example U.S. Pat. No. 3,898,084, which discloses, for example, the azo pigment chlorodiane blue in a photoconductive imaging member. The aforementioned chlorodiane blue can be prepared by azotizing dichlorobenzidine in HCl, for example 18 percent of HCl, by the addition of a sodium nitrite, followed by the addition of $HBF_4$, enabling the formation of the tetrazonium salt. This salt can then be coupled with 2-hydroxy-3-naphthanilide to permit the formation of the chlorodiane blue pigment, which formation is accomplished in the presence of sodium acetate.

U.S. Pat. No. 3,574,181 discloses disazo compounds useful as coloring agents. Composite electrophotographic photosensitive materials containing various azo compounds are disclosed in U.S. Pat. No. 4,618,672, wherein bisazo compounds particularly suitable for use in the charge generating layer of a layered electrophotographic photoconductor are illustrated. Similarly, an article by M. Hashimoto entitled "Electrophotographic Sensitivity of Fluorenone Bisazo Pigments", Electrophotography, Vol. 25, No. 3 (1986), discloses disazo compounds as charge generating materials in electrophotographic layered photoreceptors. Further, Japanese Patent Kokai No. 54-20736 discloses disazo pigments as constituents in electrophotographic processes. Japanese Patent 58-177955 also discloses many disazo compounds suitable for use in the photosensitive layer of an electrophotographic device.

U.S. Pat. No. 4,713,307, the disclosure of which is hereby totally incorporated by reference, discloses photoconductive imaging members containing a supporting substrate, certain azo pigments as photogenerating materials, and a hole transport layer that preferably contains an aryl diamine compound dispersed in an inactive resinous binder. The aforementioned azo pigments can be obtained from the couplers generated with the processes of the present invention.

U.S. Pat. No. 4,797,337, the disclosure of which is totally incorporated herein by reference, discloses a photoconductive imaging member comprising a supporting substrate, a hole transport layer, and a photogenerating layer comprising specific disazo compounds, which disazo compounds are prepared as illustrated herein, that is by the azotization and coupling reactions illustrated in the aforementioned prior art.

Additional references illustrating layered organic electrophotographic photoconductor elements with azo, bisazo, related compounds, and processes thereof include U.S. Pat. Nos. 4,390,611, 4,551,404, and 4,596,754, Japanese patent 60-64354, U.S. Pat. Nos. 4,400,455, 4,390,608, 4,327,168, 4,299,896, 4,314,015, 4,486,522, 4,486,519, 4,555,667, 4,440,845, 4,486,800, 4,309,611, 4,418,133, 4,293,628, 4,427,753, 4,495,264, 4,359,513, 3,898,084, 4,830,944, and, 4,820,602, and Japanese Patent Publication 60-111247.

In U.S. Pat. No. 4,833,052, the disclosure of which is totally incorporated herein by reference, there are illustrated certain bisazo photoconductive imaging members. Examples of bisazo compounds disclosed in this patent include those of the formulas as illustrated in column 4, such as 4,4'-bis(1"-azo-2"-hydroxy-3"-naphthanilide)-1,1'-dianthraquinonylamine.

The following United States patents are also mentioned: U.S. Pat. No. 4,830,943 relating to a photoconductor with a disazo having couplers, such as anilides, carbazole, and the like; U.S. Pat. No. 4,833,052 which discloses a photoconductive imaging member comprising a disazo compound with an azoic coupler, such as an anilide and the like, note column 7, lines 44 to 58; U.S. Pat. No. 4,868,880 which discloses a photosensitive layer comprising an azo pigment having an organic residue, see column 2, lines 53 to 65; and U.S. Pat. No. 4,830,944 which discloses a charge generation material comprising a disazo pigment with couplers, such as those derived from carboxylic acids.

SUMMARY OF THE INVENTION

It is an object of the present invention to provide certain novel anilide couplers that can be selected for the generation of red and near infrared sensitive photogenerating pigments.

Another object of the present invention is to provide economical, efficient processes for the preparation of certain anilide couplers that can be selected for the generation of red and infrared photogenerating pigments.

Another object of the present invention is to provide processes for the preparation in high yield, exceeding 75 percent, in embodiments of substantially pure anilide couplers that can be selected for the generation of azo, especially bisazo, and trisazo red and infrared photogenerating pigments.

Another object of the present invention is to provide processes for the preparation of bisazo and trisazo, photogenerating pigments, and imaging members thereof, which members can be sensitive to wavelengths of from about 650 to about 850 and preferably from about 650 to about 800 nanometers.

Another object of the present invention resides in the provision of photoresponsive imaging members which can possess excellent dark decay properties, high charge acceptance values, and electrical stability.

Further, in another object of the present invention there are provided photoconductive imaging members that are responsive to infrared light.

Additionally, another object of the present invention resides in the provision of imaging and printing methods with the photoconductive imaging members illustrated herein.

These and other objects of the present invention in embodiments thereof can be accomplished by the provision of anilide couplers and processes for the preparation thereof. More specifically, the present invention is directed to the anilide couplers from 2,8-dihydroxy-3-naphthoic acid, which anilides can be prepared as illustrated herein. The resulting anilides can be selected for the preparation of red and infrared photogenerating pigments.

Figure 1:
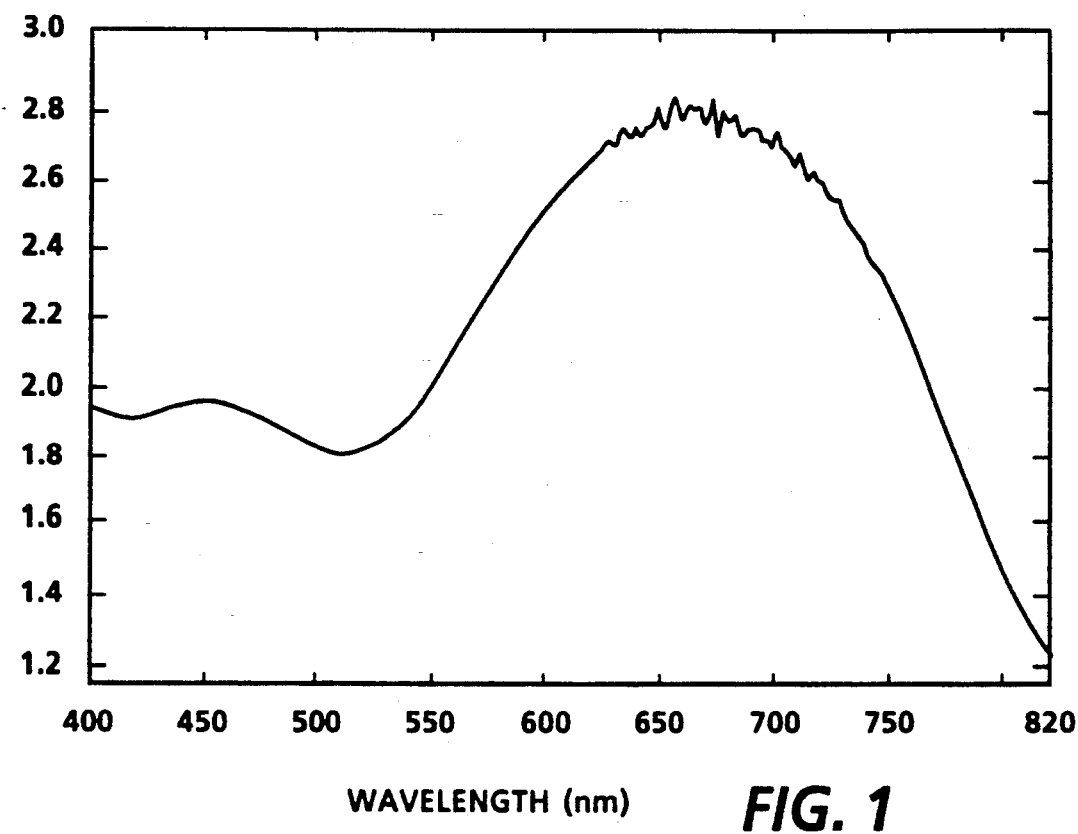
In FIGS. 1 and 3 there is illustrated the solid state absorption spectra (in KBr) of phtogenerating pigments obtained with the processes of the present invention, while in FIGS. 2 and 4 there is shown the solid state absorption spectra for the prior art photogenerating pigments prepared from a different coupler with only one hydroxy for one ring.
Figure 1A:
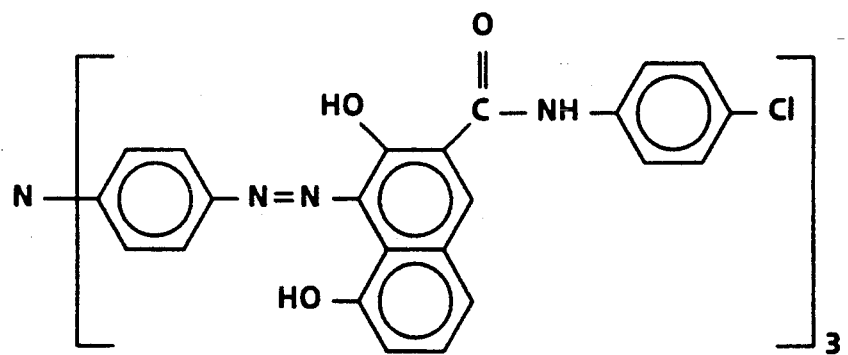
Figure 2:
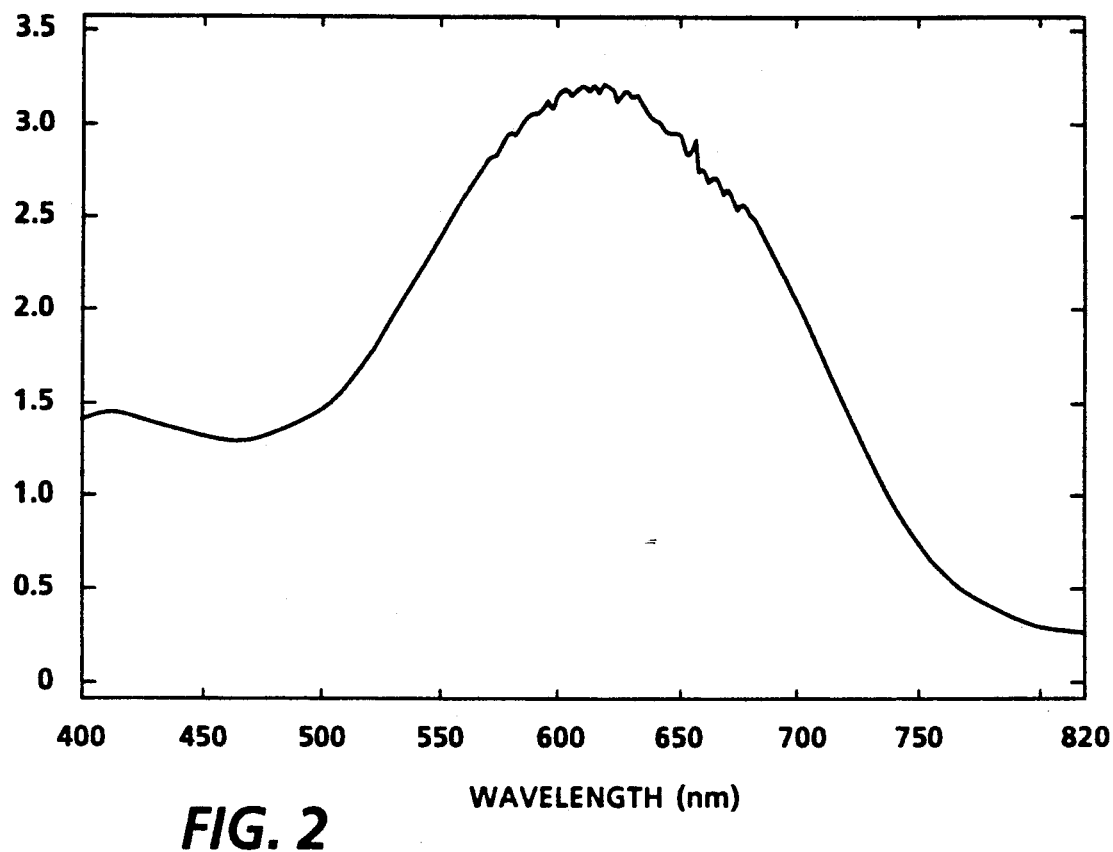
Figure 2A:
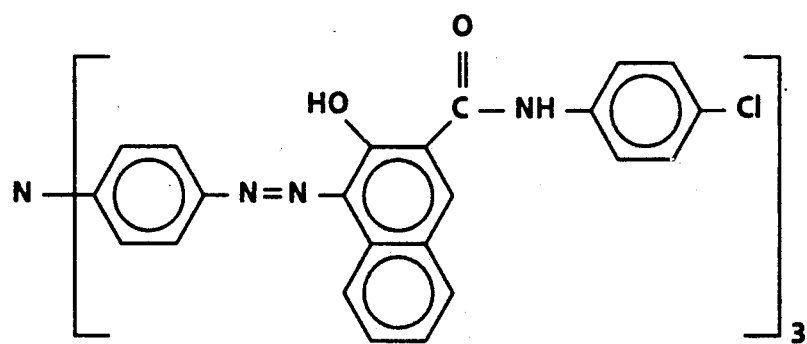
Figure 3:
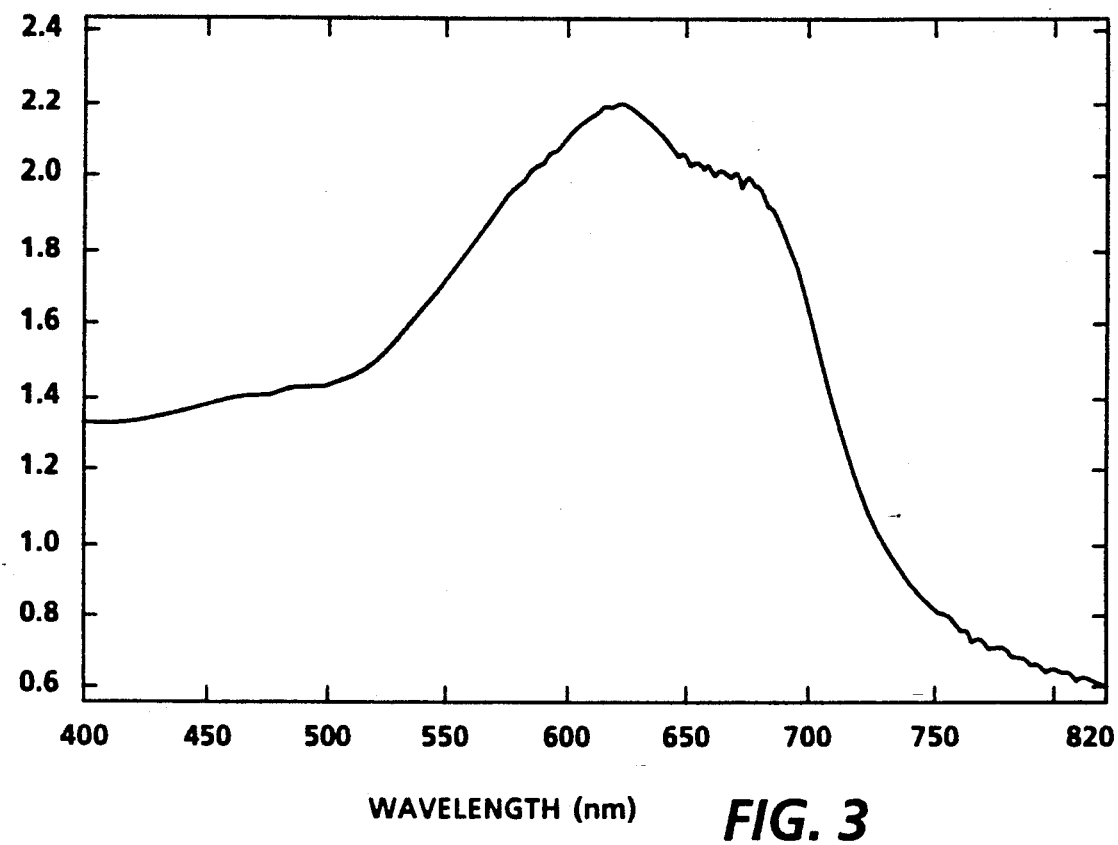
Figure 3A:
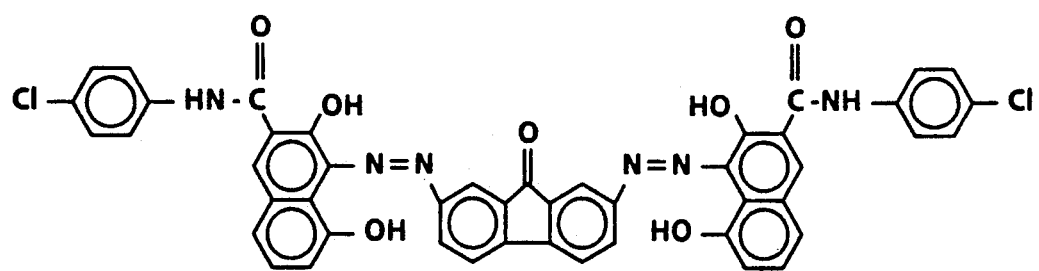
Figure 4:
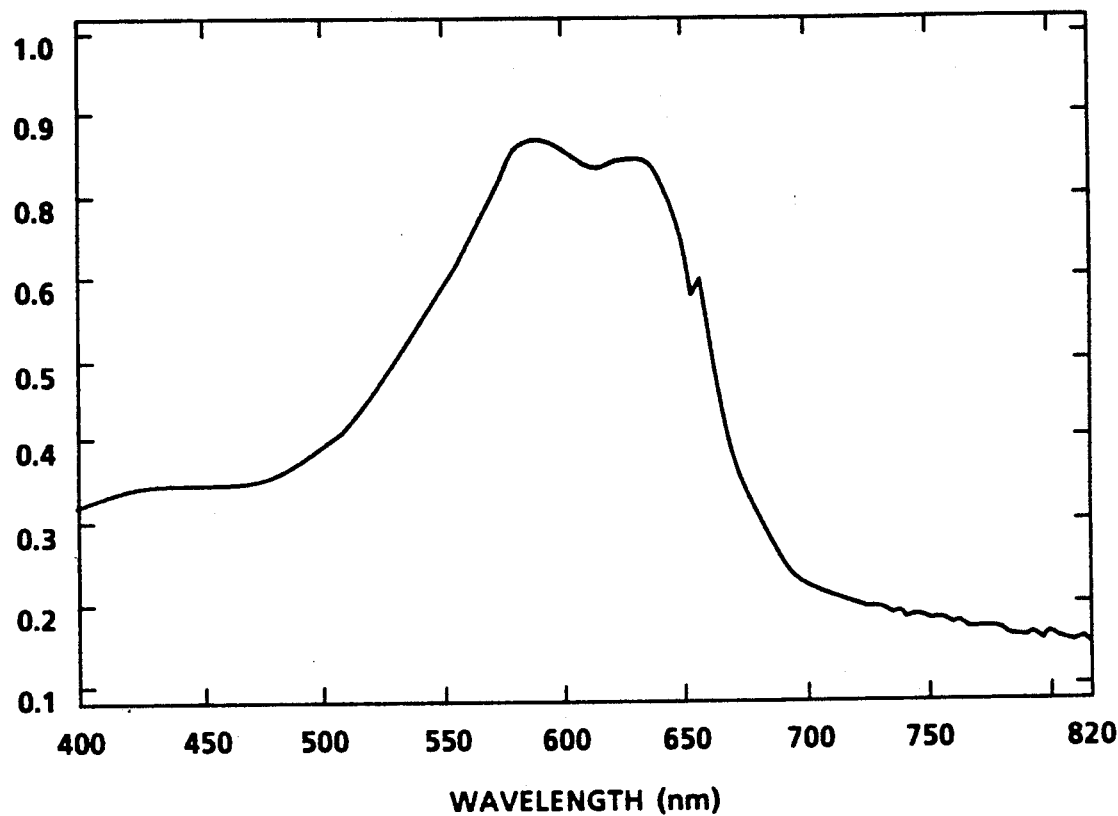
Figure 4A:
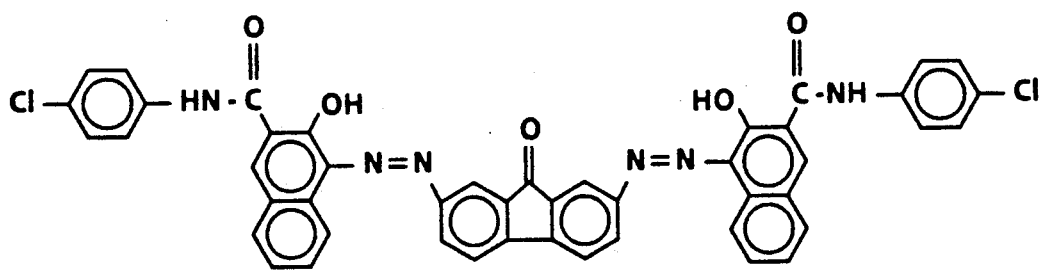

The anilide couplers and processes thereof are illustrated with reference to the following General Reaction and Specific Reaction schemes wherein Ar represents an aromatic group with from 6 to about 24 carbon atoms such as phenyl, Ar' represents an aromatic group with from 6 to about 24 carbon atoms, such as phenyl, aromatic hydrocarbons including compounds like xylene, toluene, chlorobenzene, and the like. Polar organic solvents include N,N-dimethylformamide, formamide, N,N-dimethylacetamide, methyl-N-pyrrolidinone; and ArOH such as phenol, halophenol, especially chlorophenol, and the like. Optionally, the reaction between the dihydroxy acid, the phenol and the oxyhalide can be accomplished without a hydrocarbon solvent, and wherein it is believed that phenol melts at the reaction temperature and thus can function as solvent.

GENERAL REACTION SCHEME

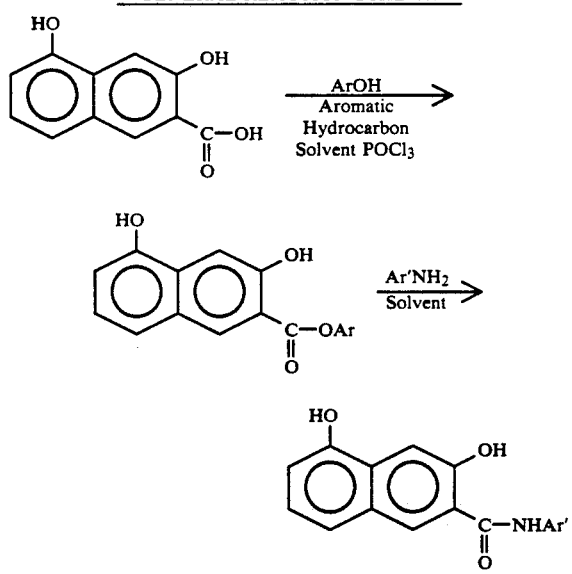

SPECIFIC REACTION SCHEME

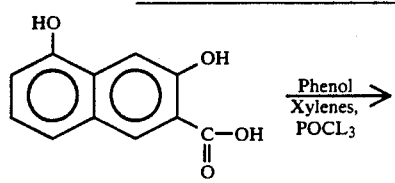

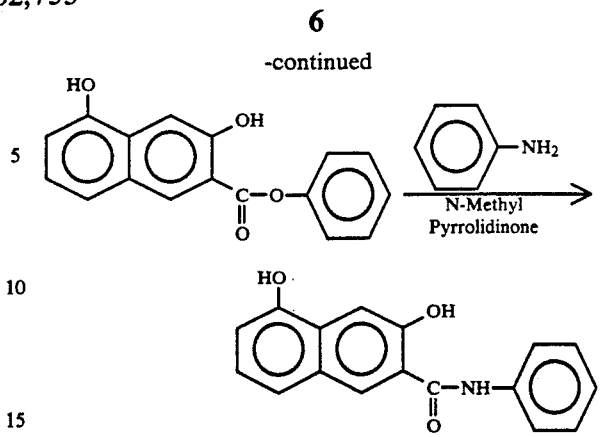

The anilide couples of the present invention can be prepared by first converting the carboxylic acid to an aromatic ester and then reacting the aromatic ester with an aniline in a solvent. More specifically, the aromatic ester can be prepared by reacting 2,8-hydroxy-3-naphthoic acid with an aromatic hydroxy compound, such as phenol, p-chlorophenol and the like, in an aromatic solvent, such as xylene or chlorobenzene. The esterification reaction can be facilitated by adding to the reaction mixture an oxyhalide, such as phosphorus oxychloride. The ratio of the acid to the aromatic hydroxy compound can be, for example, 1 to 1 depending on the reactivity of the acid and the reaction temperature. Optionally, phenol can be used as a solvent for the reaction wherein the ratio of the acid and the phenol is, for example, from about 1 to about 10. The reaction can be accomplished at effective temperature of, for example, from about 80° C. to about 200° C. After consumption of the starting acid, an aliphatic alcohol with 1 to about 12 carbon atoms, such as methanol, can be added to the reaction mixture, and the precipitated product, the aromatic ester, such as phenyl 2,8-dihydroxy-3-naphthoate, is isolated by filtration. The aromatic ester can then be purified by conventional technique, such as solvent extraction or recrystallization. The resulting product is usually pure, namely a single component is evidenced in chromatographic analysis and is characterized by m.p., IR, mass spectrometry, NMR spectroscopy, especially $^{13}C$ NMR, as well as elemental analysis.

The aromatic ester is reacted with an aniline in a solvent and heating to form the anilide product. The reaction temperature can be varied to from about 140° C. to about 280° C. or above. Specifically, phenyl 2,8-dihydroxy-3-naphthoate can be reacted with aniline in methyl N-pyrrolidinone at about 250° C. The ratio of the phenyl ester to the aniline can vary, for example, from about 1:1 equivalent and up to about 20 equivalents. After the reaction is completed, the product mixture is cooled to room temperature, about 25° C., and discharged into an acidic aqueous solution, such as a 5 percent HCl ice cold solution. The precipitated anilide product, 2,8-dihydroxy-3-naphthanilide, is isolated by filtration and washed with water. Purification can be accomplished by first dissolving the crude product in a hot solvent, such as DMF, and then precipitating the product by adding water or methanol, or a mixture of methanol and water. The purified product is then characterized by m.p., IR, mass spectrometry, NMR spectroscopy and elemental analysis.

In embodiments, the processes of the present invention comprise a first reaction of a carboxylic acid and a phenol in an aromatic solvent, which reaction is accomplished in the presence of an oxyhalide. Examples of carboxylic acids include 2,8-dihydroxy-3-naphthoic acid, and the like. Phenol reactants include halophenols, like chlorophenol, fluorophenol; alkyl phenol wherein alkyl contains from 1 to about 20 carbon atoms, like methyl phenol, ethyl phenol, naphthol, such as 1-naphthol, 2-naphthol; and alkoxy phenol with, for example, 1 to about 20 carbon atoms. A number of known aromatic solvents may be selected such as benzene, toluene, xylene, halobenzene, especially chlorobenzene, and the like. Typical reaction temperatures are from about 80 to about 200, and preferably from about 100° to about 180° C. Numerous known oxyhalides may be selected such as phosphorous oxychloride, and the like. Effective amounts of reactants include, for example, a 1:1 ratio of phenol to acid up to a 10:1 phenol to acid ratio including to about 100 milliliters per gram of acid and preferably from 0 to about 10 milliliters per gram of acid. After the reaction is completed the aromatic ester formed can be isolated by filtration and purified by conventional techniques such as solvent extraction, recrystallization, and the like.

Thereafter a second reaction is accomplished wherein the aforementioned purified ester is reacted with an aniline in a solvent to provide the desired anilide coupler product. Examples of amounts of ester and anilines include, for example, a 1:1 ratio to a 1:25 ratio with from about a 1:2 to about a 1:20 ratio being preferred. A number of known solvents can be selected, such as N,N-dimethylformamide, N,N-dimethylacetamide, N-methylpyrrolidone, and the like, and the reaction temperature can, for example, be from 140 to 280, and preferably 180° to 260° C. Ester reactant examples are as illustrated herein such as phenyl 2,8-dihydroxy-3-naphthoate, chlorophenyl 2,8-dihydroxy-3-naphthoate, methylphenyl, 2,8-dihydroxy-3-naphthoate, and the like. Aniline examples include alkylanilines like methyl aniline, ethylaniline, propylaniline, butylaniline, chloroaniline, bromoaniline, fluoroaniline; trifluoromethylanilines, nitroanilines; naphthamines, and the like.

The anilide products prepared by the processes of the present invention can be selected for the preparation of photogenerating azo pigments. The red and near infrared azo photogenerating pigments can be prepared by various suitable processes. One process embodiment involves the reaction of 2,7-diaminofluorenone with an acid such as hydrochloric acid, an alkali nitrite, such as sodium nitrite, and a precipitating agent, such as fluoboric acid, followed by isolation of the resulting tetrazonium salt. The salt can then be dissolved in a solvent, such as cold dimethylformamide containing a naphthanilide, such as 2,8-dihydroxy-3-naphthanilide, and thereafter adding an aqueous solution of an alkali, such as sodium, or potassium, acetate, heating, cooling, and isolating the product by, for example, filtration. The resulting bisazo product can be identified by melting point data, elemental analysis, infrared, X-ray, and the like. In one embodiment, the bisazos, 2,7-bis(1'-azo-2',8'-dihydroxy-3'-naphthanilide) fluorenone, can be prepared by initially tetrazotizing 2,7-diaminofluorenone with an excess amount, for example from about 2 to about 10, and preferably from about 2 to about 5 equivalents of a metallic nitrite, such as sodium nitrite, at a temperature of from about −10° to about 30° C. in an acid aqueous solution, such as a solution of hydrochloric acid. The resulting tetrazonium salts formed can be isolated as the tetrafluoroborate, or hexafluorophosphate salts by, for example, adding from about 2 to about 50, and preferably from about 10 equivalents of $HBF_4$ or $HPF_6$ to the salt solution. Thereafter, the salt can be dissolved in a solvent, such as dimethylformamide at a temperature of from about −10° to about 30° C., and the mixture resulting is allowed to react about 2 equivalents or more of an azoic coupler, such as 2,8-dihydroxy-3-naphthanilide, at a temperature of from about −10° to about 30° C. Subsequently, the desired bisazo product is precipitated out of solution by the addition of about 10 equivalents of a base, such as sodium acetate. Thereafter, the bisazo can be isolated by known means, such as filtration, and purified by solvent washings if desired. Washing can be accomplished with water for the primary purpose of removing inorganic impurities and followed by washing with dimethylformamide for the purpose of removing any organic impurities. The resulting bisazo product can be identified by melting point data, elemental analysis, infrared spectroscopy.

Another process embodiment of the present invention involves the reaction of tris(p-aminophenyl)amine with an acid such as hydrochloric acid, an alkali nitrite such as sodium nitrite, and a precipitating agent, such as fluoroboric acid, followed by isolation of the resulting hexazonium or tris(diazonium) salt. The salt can then be dissolved in a solvent, such as cold dimethylformamide containing a naphthanilide, such as 2,8-dihydroxy-3-naphtho-p-chloroanilide, and thereafter adding an aqueous solution of an alkali, such as sodium, or potassium, acetate, heating, cooling, and isolating the product by, for example, filtration. The resulting trisazo product can be identified by melting point data, elemental analysis, infrared, X-ray, and the like. In one embodiment, the trisazo compound tris[4-(1'-azo-2',8'-dihydroxy-3'-naphtho-p-chloroanilide)phenyl]amine can be prepared by initially azotizing tris(p-aminophenyl)amine with an excess amount, for example from about 2 to about 10, and preferably from about 2 to about 5 equivalents of a metallic nitrite, such as sodium nitrite, at a temperature of from about −10° to about 30° C. in an acid aqueous solution, such as a solution of hydrochloric acid. The resulting hexazonium or tris(diazonium) salts formed can be isolated as the tetrafluoroborate or hexafluorophosphate salts by, for example, adding from about 2 to about 50, and preferably from about 10 equivalents of $HBF_4$ or $HPF_6$, to the salt solution. Thereafter, the salt can be dissolved in a solvent, such as dimethylformamide, at a temperature of from about −10° to about 30° C., and the mixture resulting is allowed to react with about 3 equivalents or more of an azoic coupler 2,8-dihydroxy-3-naphtho-p-chloroanilide at a temperature of from about −10° to about 30° C. Subsequently, the desired trisazo product is precipitated out of solution by the addition of about 10 equivalents of a base, such as sodium acetate. Thereafter, the trisazo can be isolated by known means, such as filtration, and purified by solvent washings if desired. Washing can be accomplished with water for the primary purpose of removing inorganic impurities and followed by washing with dimethylformamide for the purpose of removing any organic impurities. The resulting trisazo product can be identified by melting point data, elemental analysis, and infrared spectroscopy.

With respect to the preparation of other photogenerating bis and trisazo pigments, other couplers, such as 2,8-dihydroxy-3-naphtho-p-fluoroanilide; 2,8-dihydroxy-3-naphtho-o-ethylanilide; 2,8-dihydroxy-3-naphtho-o-chloroanilide; 2,8-dihydroxy-3-naphtho-o-fluoroanilide; 2,8-dihydroxy-3-naphtho-p-trifluoromethylanilide; 2,8-dihydroxy-3-naphtho-m-nitroanilide; 2,8-dihydroxy-3-naphtho-p-methylanilide; 2,8-dihydroxy-3-naphtho-p-methoxyanilide; and the like may be selected.

The photogenerating compounds of the present invention in embodiments thereof enable enhanced photosensitivity in the red and infrared wavelength range. In particular, imaging members with photosensitivity at wavelengths of up to about 800 nanometers are provided in embodiments of the present invention, which renders them particularly useful for imaging and printing applications such as LED and diode laser printing processes, which typically require sensitivity of about 600 to about 800 nanometers.

The present invention also encompasses a method of generating images with the photoconductive imaging members disclosed herein. The method comprises the steps of generating an electrostatic latent image on a photoconductive imaging member of the present invention, developing the latent image, and transferring the developed electrostatic image to a substrate. Optionally, the transferred image can be permanently affixed to the substrate. Development of the image may be achieved by a number of methods, such as cascade, touchdown, powder cloud, magnetic brush, and the like. Transfer of the developed image to a substrate may be by any method, including those making use of a corotron or a biased roll. The fixing step may be performed by means of any suitable method, such as flash fusing, heat fusing, pressure fusing, vapor fusing, and the like. Any material used in xerographic copiers and printers may be used as a substrate, such as paper, transparency material, or the like.

Specific embodiments of the invention will now be described in detail. These Examples are intended to be illustrative, and the invention is not limited to the materials, conditions, or process parameters set forth in these embodiments. All parts and percentages are by weight unless otherwise indicated.

EXAMPLE I

Synthesis of Phenyl 2,8-Dihydroxy-3-naphthoate 2,8-Dihydroxy-3-naphthoic (50 grams, 0.24 mole), phenol (184.5 grams, ~2 moles) and phosphorus oxychloride (40 grams) were mixed inside a 500 milliliter round bottom flask. The mixture was stirred and heated by an oil bath (bath temperature ~125° C.) for 2 hours under an $N_2$ atmosphere. TLC analysis revealed that the starting acid was consumed. The product mixture was cooled to room temperature and 80 milliliters of methanol were introduced. The resulting methanolic solution was poured into a 2 liter beaker containing 1 liter of water. After about 1.5 hours of continuous stirring, the desirable product was solidified. The crude product was isolated by filtration. It was purified by first washing three times with water, then reprecipitating from a mixture of methanol and water (100 milliliters of methanol and 800 milliliters of water) and then washing two times with chloroform (150 milliliters each), yielding pure phenyl 2,9-dihydroxy-3-naphthoate, 52 grams (76 percent).

| | |
|---|---|
| m.p.: | 172 to 173.5° C. |
| IR(KBr): | 1,691 cm$^{-1}$ (C = O) |
| Calculated for $C_{17}H_{12}O_4$: | C 72.86, H 4.31 |
| Found: | C 72.91, H 4.59 |

EXAMPLE II

Synthesis of 2,8-Dihydroxy-3-naphthanilide

Phenyl 2,8-dihydroxy-3-naphthoate (20 grams, 0.07 mole), aniline (39.7 grams, 0.42 mole) and 10 milliliters of N-methyl pyrrolidinone were charged into a 100 milliliter 3-necked flask, which was equipped with a magnetic stirrer and a nitrogen inlet. The mixture was stirred and was heated to reflux at a bath temperature of ~250° C. under an $N_2$ atmosphere. After 2 hours, TLC analysis revealed that all the starting phenyl ester was consumed. The mixture was cooled to room temperature and was poured into an 800 milliliter beaker containing ~300 milliliters of ice cold 5 percent HCl. The yellow precipitate obtained was isolated by filtration. After washing with water and vacuum drying, ~5.5 grams of crude product were resulted. It was then recrystallized from a mixture of DMF/MeOH/H$_2$O, yielding 4.99 grams (89 percent) of a yellow solid, which was subsequently identified as 2,8-dihydroxy-3-naphthanilide.

| | |
|---|---|
| m.p.: | 258 to 260° C. |
| IR(KBr) | 1,660 and 1,667 cm$^{-1}$ |
| Calculated for $C_{17}H_{13}NO_3$: | C 73.11, H 4.69, N 5.02 |
| Found: | C 72.29, H 4.92, N 5.04 |

EXAMPLE III 2,8-Dihydroxy-3-naphtho-p-chloroanilide, 2,8-dihydroxy-3-naphtho-p-fluoroanilide and 2,8-dihydroxy-3-naphtho-o-ethylanilide were prepared by repeating the procedures of Example II with the exceptions that there were selected as aniline reactants, p-chloroanilide, p-fluoroanilide and o-ethylanilide.

| 2,8-dihydroxy-3-naphtho-p-chloroanilide, yield 97 percent, | |
|---|---|
| m.p.: | 255 to 257° C. |
| IR(KBr): | 1,660 and 1,665 cm$^{-1}$ |
| Calculated for $C_{17}H_{12}NO_3Cl$: | C 65.08, H 3.86, N 4.46 |
| Found: | C 64.74, H 4.14, N 4.58 |
| 2,8-dihydroxy-3-naphtho-p-fluoroanilide, yield 96 percent, | |
| m.p.: | 236 to 239° C. |
| IR(KBr): | 1,658 cm$^{-1}$ |
| 2,8-dihydroxy-3-naphtho-o-ethylanilide, yield 91 percent, | |
| m.p.: | 178 to 180° C. |
| IR(KBr): | 1,650 cm$^{-1}$ |
| Calculated for $C_{19}H_{17}NO_3$: | C 74.25, H 5.58, N 4.56 |
| Found: | C 75.25, H 5.91, N 4.74 |

EXAMPLE IV 2,7-Diaminofluorenone, 1.05 gram, 5 millimoles, was stirred in 20 milliliters of 18 percent hydrochloric acid at about 50° to 60° C. for about one hour and then at room temperature, about 25° C., overnight, 18 hours. The yellow dispersion obtained was then cooled to about 0° to 5° C. by an ice water bath. A cold aqueous solution of NaNO$_2$ (1 gram in 2.5 milliliters of water) was then added dropwise in about 15 minutes to the aforementioned yellow dispersion. After the addition of the NaNO$_2$ solution, the resulting mixture was stirred in an ice bath for 30 minutes. A clear dark brown solution resulted. This dark brown solution was filtered by a medium sintered glass funnel into a 250 milliliter precooled filtration flask. Fluoroboric acid, 10 milliliters, was added to the cold filtrate and a yellow precipitate was formed immediately. This mixture of the filtrate and fluoroboric acid was stirred at ice cold temperature for about 30 minutes. The yellow precipitate was collected by filtration. After washing with cold water, cold methanol and ether, the product was air dried for 1 hour, yielding the tetrazonium salt fluorenone-2,7-tetrazonium bis(tetrafluoroborate), about 1.85 grams.

The above prepared tetrazonium salt was then dissolved in about 40 milliliters of cold DMF solvent inside a 3-neck 1 liter flask surrounded by an ice water bath. A cold DMF solution containing 3.46 grams of the coupler, 2,8-dihydroxy-3-naphthanilide, synthesized by the process of Example II in 250 milliliters of DMF, was then added into the salt solution in about 20 minutes. The color of the salt solution changed from orange brown to dark purple. A cold solution of 5 grams of NaOAc in 75 milliliters of water was added slowly into the DMF solution (in 30 minutes). The temperature of the DMF solution was kept below 7° C. during the addition. After the addition was completed, the ice bath was removed and the product mixture was stirred at room temperature overnight, about 18 hours. Crude bisazo pigment product was isolated by filtration (fine sintered glass funnel). The crude product was then transferred to a 750 milliliter beaker and was stirred with about 250 milliliters of water at about 81° C. for 2½ hours, overnight (18 hours) and then 2½ hours. After the third DMF wash, the pigment product was stirred in 250 milliliters of acetone and then 250 milliliters of ether (2½ hours each) to remove residual high boiling solvents of water and DMF, and the product was then dried inside a vacuum oven at 75° C. at 1.5 to 2.0 millimeters of mercury for 16 hours. A dark blue pigment product, 0.51 gram, about 13 percent yield, which was identified as 2,7-bis(1'-azo-2',8'-dihydroxy-3'-naphthanilide)-fluorenone, was obtained.

| m.p.: | >300° C. |
|---|---|
| IR(KBr) | 1,720 (fluorenone C = O), 1,677 cm$^{-1}$ (amide C = O). |
| Calculated for C$_{47}$H$_{30}$N$_6$O$_7$: | C 71.39, H 3.82, N 10.62 |
| Found: | C 70.19, H 4.22, N 10.31 |

An imaging member was prepared with the above prepared azo photogenerating pigment. To a 1 ounce amber bottle there were added 52.8 milligrams of polyvinyl formal (obtained from Scientific Polymer Products, Inc., formal content 82 percent, acetate content 12 percent, hydroxy content 6 percent) and 10 milliliters of tetrahydrofuran. To the bottle was then added 211.1 grams of the bisazo pigment and about 90 grams of steel shot (1/8 inch diameter, number 302 stainless steel shot). The bottle was then placed on a Red Devil Paint Conditioner (Model 5100X) and shaken for about 30 minutes. The resulting dispersion was coated onto a 7.5 inch by 10 inch brush grained aluminum substrate obtained from Ron Ink Company using a Gardner Mechanical Drive with a 6 inch wide Bird Film Application (0.5 mil wet gap) inside a humidity-controlled glove box. The relative humidity of the glove box was controlled by dry air to about less than 25 percent. The resulting charge generation layer was air dried for about 30 minutes and then vacuum dried for about 1 hour at 100° C. The thickness of the charge generator layer was estimated to be about 0.4 micron from TEM micrographs.

The above charge generator layer was overcoated with a charge transport layer prepared as follows. A solution containing 4.2 grams of MAKROLON® a polycarbonate resin obtained from Larbensabricken Bayer A.G., 2.8 grams of N,N'-bis(3"-methylphenyl)-1,1'-biphenyl-4,4'-diamine prepared as disclosed in U.S. Pat. No. 4,265,990, the disclosure of which is totally incorporated herein by reference, was prepared by dissolving the above materials in 31 milliliters of methylene chloride inside a 2 ounce amber bottle. The transport layer was obtained by coating the solution onto the charge generator layer using a 3.5 inch wide, 5 mil wet gap Bird Film Applicator, resulting in a transport layer about 27 microns thick. The resulting photoconductive device was air dried for about 1 hour and vacuum dried at 100° C. for about 16 hours before electrical testing.

The imaging member thus prepared was evaluated as follows. Xerographic measurements were made on a flat plate scanner using 2 inch by 2.5 inch samples of the imaging member prepared as described herein. The surface potential of the device was monitored with a capacitively coupled ring probe connected to a Keithley electrometer (Model 610C) in the coulomb mode. The output of the electrometer was displayed on a strip-chart recorder (HP Model 740A) which was calibrated by applying known voltage on an uncoated aluminum substrate. The exposure wavelength and the intensity were selected and adjusted using interference and neutral density filters, respectively. With the shutter closed, the dark decay was measured. With the shutter open, the photosensitivity at a known light exposure was recorded. The imaging member was charged to about $-1,000$ volts at the peak voltage and was allowed to discharge in the dark for 2 to 3 seconds to determine the dark decay. Subsequently, the imaging member was exposed to an erase lamp to photodischarge the surface charge and to determine its residual voltage ($V_R$). Thereafter, the imaging member was charged in a similar manner and exposed to visible radiation at the dark development potential ($V_{ddp}$), and the sensitivity of the member was determined in terms of $E_{\frac{1}{2}}$, which represents the energy required to discharge half of the dark development potential. The imaging member exhibited a dark development potential ($V_{ddp}$) of $-990$ volts, a dark decay of $-8$ volts per second, an $E_{\frac{1}{2}ddp}$, the energy to discharge half the potential at 600 nanometers (erg/cm$^2$), of 30.

EXAMPLE V

Other bisazo pigments from 2,7-diaminofluorenone, such as 2,7-bis(1'-azo-2',8'-dihydroxy-3'-naphtho-p-chloroanilide)fluorenone and 2,7-bis(1'-azo-2',8'-dihydroxy-3'-naphtho-o-ethylanilide)fluorenone, were prepared by repeating the procedures in Example IV with the exceptions that there were selected as coupler components 2,8-dihydroxy-3-naphtho-p-chloroanilide and 2,8-dihydroxy-3-naphtho-o-ethylanilide.

2,7-bis(1'-azo-2,8-dihydroxy-3'-naphtho-p-chloroanilide)fluorenone, yield 7 percent:

| m.p.: | 267° C. (dec.) |
|---|---|
| IR(KBr) | 1,718 (fluorenone C = O) and 1,677 (amide C = O) |

-continued

| Calculated for $C_{47}H_{28}N_6O_7Cl_2$: | C 65.67, H 3.28, N 9.78 |
|---|---|
| Found: | C 64.70, H 2.98, N 9.13 |

2,7-bis(1'-azo-2',8'-dihydroxy-3'-naphtho-o-ethylanilide)fluorenone, yield 8 percent:

| m.p.: | >300° C. |
|---|---|
| IR(KBr) | 1,719 (fluorenone C = O) and 1,678 (amide C = O) |
| Calculated for $C_{51}H_{38}N_6O_7$: | C 72.33, H 4.52, N 9.92 |
| Found: | C 70.89, H 4.39, N 9.33 |

Imaging members were then prepared with these pigments by repeating the procedures of Example IV. The results are as follows:

2,7-bis(1'-azo-2',8'-dihydroxy-3'-naphtho-p-chloroanilide)fluorenone

| maximum charge acceptance: | −850 volts |
|---|---|
| $V_{ddp}$: | −700 volts |
| dark decay: | −70 volts/second |
| $E_{0.5}$ at 600 nanometers | 18 ergs/cm$^2$ |

2,7-bis(1'-azo-2',8'-dihydroxy-3'-naphtho-o-ethylanilide)fluorenone

| maximum charge acceptance: | −1,000 volts |
|---|---|
| $V_{ddp}$: | −940 volts |
| dark decay: | −30 volts/second |
| $E_{0.5}$ at 600 nanometers | 25 ergs/cm$^2$ |

EXAMPLE VI

Tris(4-aminophenyl)amine (0.58 gram, 2 millimoles) was stirred in an aqueous solution containing 14 milliliters of 18 percent hydrochloric acid at about 60° C. for 1 hour and then 16 hours at room temperature. The dispersion obtained was then cooled to 0° to 5° C. by an ice water bath. A cold aqueous solution of sodium nitrite (0.6 gram in 1.5 milliliters) was added dropwise. After the addition, the resulting mixture was stirred in an ice bath for another 30 minutes. A clear brown solution resulted. The dark brown solution was filtered (by a medium sintered glass funnel) into a 250 milliliter precooled filtration flask. Fluoroboric acid (5 milliliters) was added to the cold filtrate and a yellow precipitate was formed. This mixture was stirred at ice cold temperature for another 30 minutes. The yellow precipitate was collected by filtration. After washing with cold water, cold methanol and ether, about 1.25 grams of a tris(diazonium)salt was obtained after drying, IR(KBr): 3,118(C-H) and 2,300 cm$^{-1}$

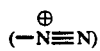

The tris(diazonium)salt was dissolved in about 30 milliliters of cold DMF in a 1 liter 3-neck flask, which was surrounded by an ice water bath. A cold DMF solution containing 2.08 grams (6.6 millimoles) of 2,8-dihydroxy-3-naphtho-p-chloroanilide, prepared as in Example III, in about 120 milliliters of DMF was added into the salt solution. A cold aqueous solution of 3 grams of NaOAc in 45 milliliters of water was added in 30 minutes. The temperature of the DMF solution was kept below 7° C. during the addition. After the addition was completed, the ice bath was removed and the product was stirred at room temperature for 16 hours. Crude pigment was isolated by filtration (fine sintered glass funnel). The crude product was then purified by washing with warm water (2×250 milliliters at 80° C.), warm DMF (3×250 milliliters at 80° C), acetone and ether, yielding a dark blue pigment, which was identified as tris[4-(1'-azo-2',8'-dihydroxy-3'-naphtho-p-chloroanilide)phenyl]amine, 1.19 grams, yield 47 percent.

| m.p.: | 272° C. (dec.) |
|---|---|
| IR(KBr): | 1,678 cm$^{-1}$ (amide C = O) |
| Calculated for $C_{69}H_{95}N_{10}O_9Cl_3$: | C 65.54, H 3.59, N 11.08 |
| Found: | C 64.70, H 3.85, N 10.29 |

An imaging member was prepared with the above pigment using the procedures described in Example IV. The results were:

| maximum charge acceptance: | −950 volts |
|---|---|
| $V_{ddp}$: | −800 volts |
| dark decay: | −35 volts/second |
| $E_{0.5}$ at 600 nanometers | 55 ergs/cm$^2$ |
| $E_{0.5}$ at 790 nanometers | 45 ergs/cm$^2$ |

From absorption spectra it can be determined that the hydroxy group on the eighth position of the coupler enables a wavelength extension of approximately 50 nanometers. More specifically, bisazo pigments prepared, for example, from 2,7-diaminofluorene and trisazo obtained from tris(4-aminophenyl) amine have an increase in absorption of light in the red and infrared regions of about 50 nanometer extension as determined from the absorption spectrum thereof in view, it is believed, because of the presence of hydroxy groups, intramolecular hydrogen bonding, for example, between the hydroxy group at the eighth position with the azo linkage.

Other modifications of the present invention will occur to those of ordinary skill in the art subsequent to a review of the present application. These modifications, and equivalents thereof are intended to be included within the scope of this invention.

What is claimed is:

1. The anilide coupler of the formula

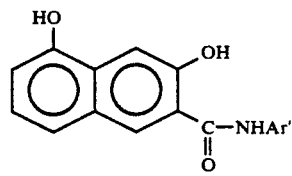

wherein Ar' is an aromatic group.

2. An anilide coupler in accordance with claim 1 wherein Ar' is an aromatic group with from 6 to about 24 carbon atoms.

3. An anilide coupler in accordance with claim 1 wherein Ar' is phenyl.

4. An anilide coupler in accordance with claim 1 of the formula

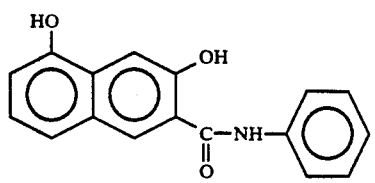

5. The anilide couplers 2,8-dihydroxy-3-naphtho-p-fluoroanilide; 2,8-dihydroxy-3-naphtho-o-ethylanilide; 2,8-dihydroxy-3-naphtho-o-chloroanilide; 2,8-dihydroxy-3-naphtho-o-fluoroanilide; 2,8-dihydroxy-3-naphtho-p-trifluoromethylanilide; 2,8-dihydroxy-3-naphtho-m-nitroanilide; 2,8-dihydroxy-3-naphtho-p-methylanilide; or 2,8-dihydroxy-3-naphtho-p-methoxyanilide.

6. An anilide copuler in accordance with claim 2 wherein said coupler is 2,8-dihydroxy-3-naphtho-p-chloro anilide.

* * * * *